US009579067B2

(12) United States Patent
Thompson

(10) Patent No.: US 9,579,067 B2
(45) Date of Patent: Feb. 28, 2017

(54) DETECTION OF A LEADING STROKE RISK INDICATOR

(71) Applicant: Jonathan Moisant Thompson, Santa Clara, CA (US)

(72) Inventor: Jonathan Moisant Thompson, Santa Clara, CA (US)

(73) Assignee: Intel Corporation, Santa Clara, CA (US)

( * ) Notice: Subject to any disclaimer, the term of this patent is extended or adjusted under 35 U.S.C. 154(b) by 240 days.

(21) Appl. No.: 14/125,422

(22) PCT Filed: Jun. 26, 2013

(86) PCT No.: PCT/US2013/047947
§ 371 (c)(1),
(2) Date: Dec. 11, 2013

(87) PCT Pub. No.: WO2014/209303
PCT Pub. Date: Dec. 31, 2014

(65) Prior Publication Data
US 2015/0005645 A1    Jan. 1, 2015

(51) Int. Cl.
*A61B 5/00*    (2006.01)
*A61B 5/02*    (2006.01)

(52) U.S. Cl.
CPC .......... *A61B 5/7246* (2013.01); *A61B 5/004* (2013.01); *A61B 5/0013* (2013.01);
(Continued)

(58) Field of Classification Search
CPC ... A61B 5/0013; A61B 5/004; A61B 5/02007; A61B 5/7235; A61B 5/7246; A61B 5/7275; A61B 5/7282
See application file for complete search history.

(56) References Cited

U.S. PATENT DOCUMENTS

2008/0045847 A1* 2/2008 Farag ................. A61B 5/02055
                                                      600/500
2013/0331664 A1* 12/2013 Gilad-Gilor ............. A61B 5/00
                                                      600/301
(Continued)

FOREIGN PATENT DOCUMENTS

JP    2006305260 A    11/2006
JP    2007295946 A    11/2007
(Continued)

OTHER PUBLICATIONS

"Japanese Application Serial No. 2016-516494, Office Action mailed Nov. 22, 2016", W/ English Translation, 10 pgs.

*Primary Examiner* — Ruth S Smith
(74) *Attorney, Agent, or Firm* — Schwegman Lundberg & Woessner, P.A.

(57)    ABSTRACT

Embodiments of a system and method for detecting a leading stroke risk indicator using low-cost, non-contact visual computing methods are generally described herein. In some embodiments, a video camera is arranged to capture a video of a face of a subject to be evaluated for having a stroke risk indicator. A memory is provided for storing data. A processor is coupled to the memory and is arranged to analyze processed image data associated with the video of the face of the subject captured by the video camera. The processor is further arranged to determine whether the processed image data exhibits a leading indicator for carotid artery stenosis.

20 Claims, 10 Drawing Sheets

(52) U.S. Cl.
CPC ........ *A61B 5/02007* (2013.01); *A61B 5/7235* (2013.01); *A61B 5/7275* (2013.01); *A61B 5/7282* (2013.01)

(56) References Cited

U.S. PATENT DOCUMENTS

| | | | |
|---|---|---|---|
| 2013/0345524 A1* | 12/2013 | Meyer | G06F 19/363 600/301 |
| 2014/0046192 A1* | 2/2014 | Mullin | H05K 13/00 600/474 |
| 2014/0249398 A1 | 9/2014 | Morris et al. | |

FOREIGN PATENT DOCUMENTS

| | | | |
|---|---|---|---|
| JP | 2010187928 A | 9/2010 | |
| JP | 2014198201 A | 10/2014 | |
| JP | 2014529797 A | 11/2014 | |

* cited by examiner

DETECTION OF A LEADING STROKE RISK INDICATOR

PRIORITY APPLICATION

This application is a U.S. National Stage Application under 35 U.S.C. 371 from International Application No. PCT/US2013/047947, filed Jun. 26, 2013, which is hereby incorporated by reference in its entirety.

BACKGROUND

From the heart, there are two carotid arteries that split off after leaving the heart and form symmetric arrangements through the neck to feed the left and right sides of the face and brain. One risk factor for stroke in adult patients is the presence of a condition called carotid artery stenosis, which is a blockage or narrowing of the blood vessels that feed the brain. Buildup commonly occurs where the internal and external carotid arteries diverge in the neck, prior to the blood's arrival to the face.

The blockage or narrowing of the blood vessels that feed the brain tends to build up over time and can lead to strokes in two ways. First, an ischemic stroke may occur, wherein plaque in the artery causes a clot to accumulate over time until the clot fully blocks normal blood flow and deprives the brain of oxygenated blood. In contrast, an embolic stroke involves an accumulated clot becoming dislodged and traveling along with the blood further into the brain until it becomes lodged in a smaller vessel and blocks the blood flow.

Preventative screening for asymptomatic stenosis is currently not a recommendation. However, this leaves patients at risk until the first event occurs.

DETAILED DESCRIPTION

Embodiments described herein enable identification of early buildup in the carotid arteries that may lead to carotid artery stenosis. Early detection allows a subject, such as a patient, a person forming a self-evaluation, someone being evaluated by another, etc., to visit a doctor for verification prior to the subject experiencing a cerebrovascular attack, which commonly referred to as having a stroke. Subjects may not exhibit any other symptoms that would put them at risk for strokes. Thus, the process according to an embodiment allows for non-invasive identification of moderate to severe stenosis at negligible cost. Identification of moderate to severe stenosis is a leading indicator for strokes. In the healthcare field, leading indicators involve a phenomenon that generally occurs in advance of some other phenomenon and aids in prediction of the later occurring phenomenon, e.g., high cholesterol for heart attacks. Such leading indicators are used to forecast the likelihood of disease and/or medical conditions. Accordingly, detection of carotid artery stenosis through video detection of pulse phase offset/shift between opposing sides of a subject's face may be used as a risk indicator for strokes. By identifying moderate to severe stenosis using a non-invasive technique, a user may be able to identify a potentially serious condition before a stroke event occurs.

Preventative screening for asymptomatic stenosis is currently not a recommended procedure absent a stroke or other event reported by the subject, e.g., sudden numbness or weakness of the face, arm or leg, especially on one side of the body, confusion, trouble speaking or understanding, trouble seeing in one or both eyes, trouble walking, dizziness, loss of balance or coordination, severe headache with no known cause, etc. Without prophylactic screening, potential stroke victims are left at risk until their first event occurs: The United States (US) Preventative Services Task Force currently advises against preventative screening for stenosis in subjects who do not exhibit any other warning signs. This means that otherwise diagnosable conditions can persist and are examined only after the first stroke event has occurred. Embodiments described herein provide a method that allows for non-invasive identification of moderate to severe stenosis at negligible cost, thereby alerting a user to have a potentially serious condition examined before a stroke event occurs.

Figure 1:
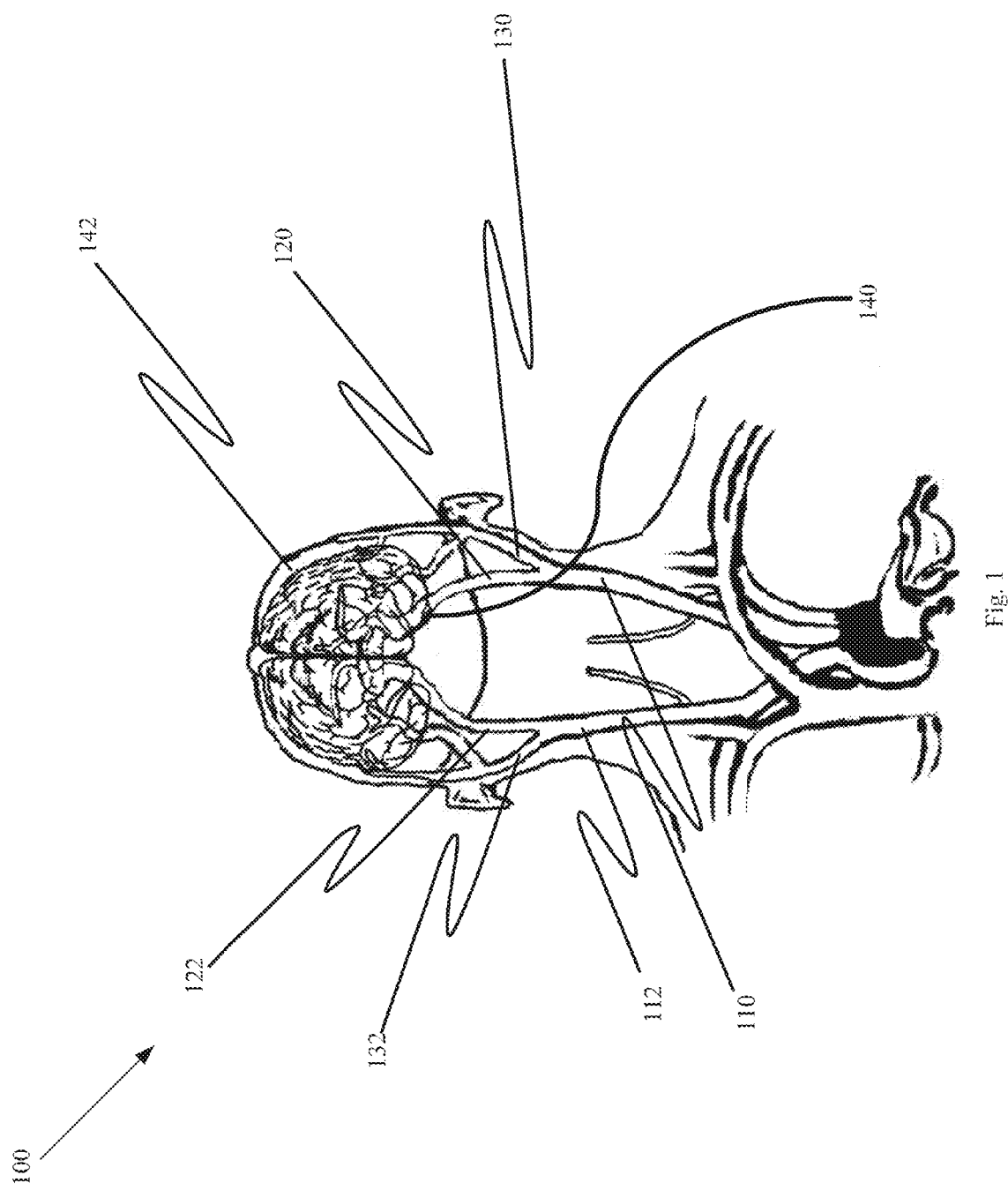
FIG. 1 illustrates a cross-section of a head including the carotid arteries according to an embodiment.

FIG. 1 illustrates a cross-section of a head 100 including the carotid arteries. In FIG. 1, the two halves of the head are each fed by their own carotid artery, e.g., left common carotid 110 and right common carotid 112. The left common carotid artery 110 and the right common carotid artery 112 each split into an internal carotid artery 120, 122 and an external carotid artery 130, 132. The internal carotid arteries 120, 122 provide blood flow to the brain 140. The external carotid arteries 130, 132 provide blood flow to the face 142.

The left common carotid 110 and right common carotid 112 have independent risks of developing a stenosis condition. Moreover, there may be stenosis on one side but not on the other. If a buildup occurs on one side, there will be noticeably asymmetric cardiac activity downstream from that blockage when compared to the other side, which may be unblocked.

Figures 2A, 2B, 2C:
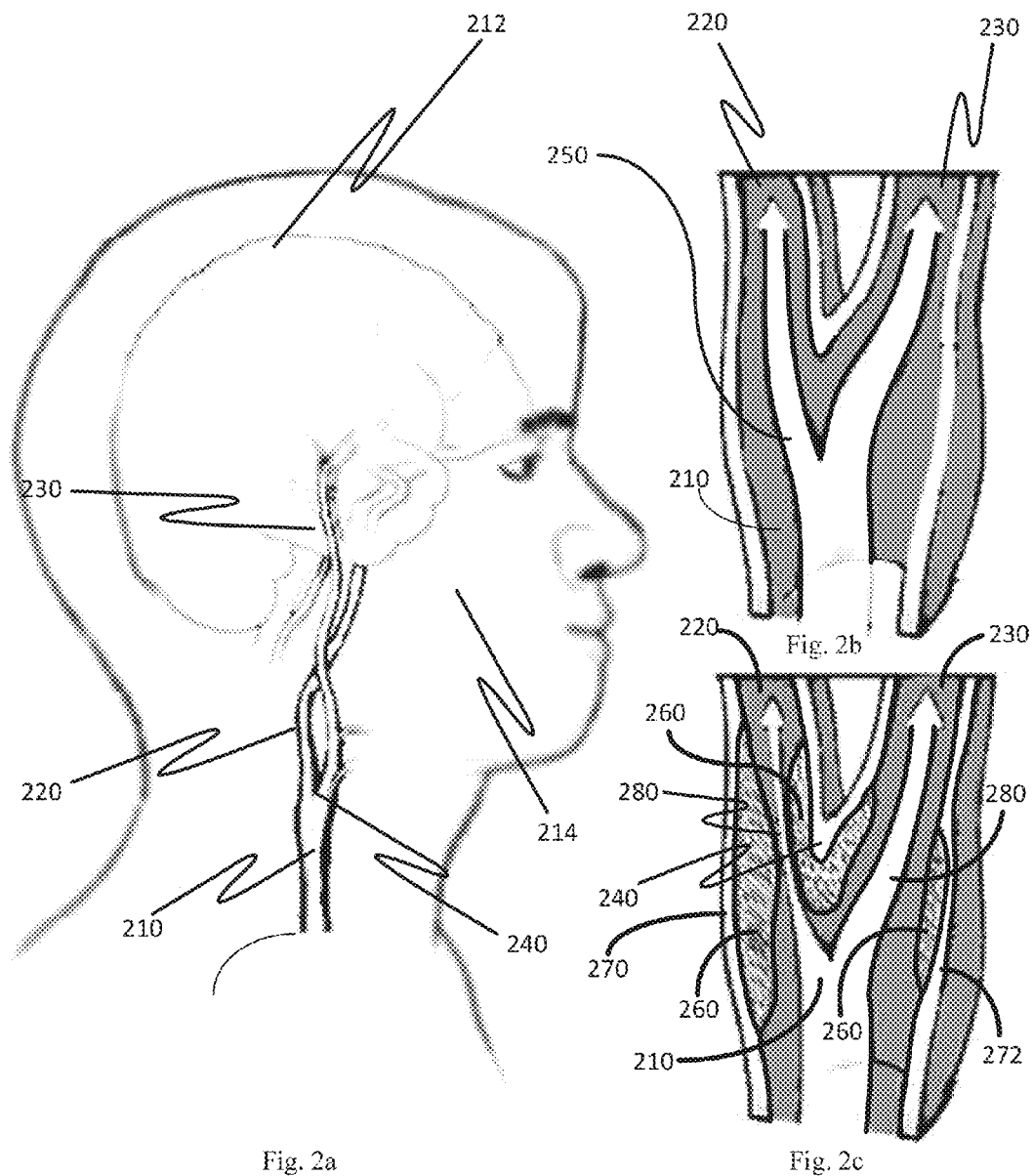
FIGS. 2a-c illustrate the division of the internal and external carotid arteries according to an embodiment.

FIGS. 2a-c illustrate the division of the internal and external carotid arteries. FIG. 2a shows the right common carotid artery 210 leading to the brain 212 and face 214. Buildup of the left common carotid (not shown in FIGS. 2a-c) and/or right common carotid artery 210 commonly occurs where the internal carotid artery 220 and external carotid artery 230 diverge, e.g., bifurcate, in the neck prior to the blood's arrival to the brain 212 and face 214.

FIG. 2b shows a close-up view of a common carotid artery 210. In FIG. 2b, the common carotid artery 210 splits into the internal carotid artery 220 and the external carotid artery 230. FIG. 2b shows normal blood flow 250 from the common carotid artery 210 into the internal carotid artery 220 and the external carotid artery 230.

FIG. 2c illustrates buildup 260 in the common carotid artery 210. The buildup 260 is shown along the exterior walls 270, 272 of the common carotid artery 210. Buildup 260 is also shown at the common carotid bifurcation 240 where the common carotid artery 210 branches into the internal carotid artery 220 and the external carotid artery 230. As a result of the buildup 260 at the exterior walls 270, 272 of the common carotid artery and at common carotid bifurcation 240, the blood flow 280 is shown to be reduced into each of the internal carotid artery 220 and the external carotid artery 230. However, those skilled in the art will recognize that the buildup may affect the internal carotid artery 220 or the external carotid artery 230 without affecting the other.

Figure 3:
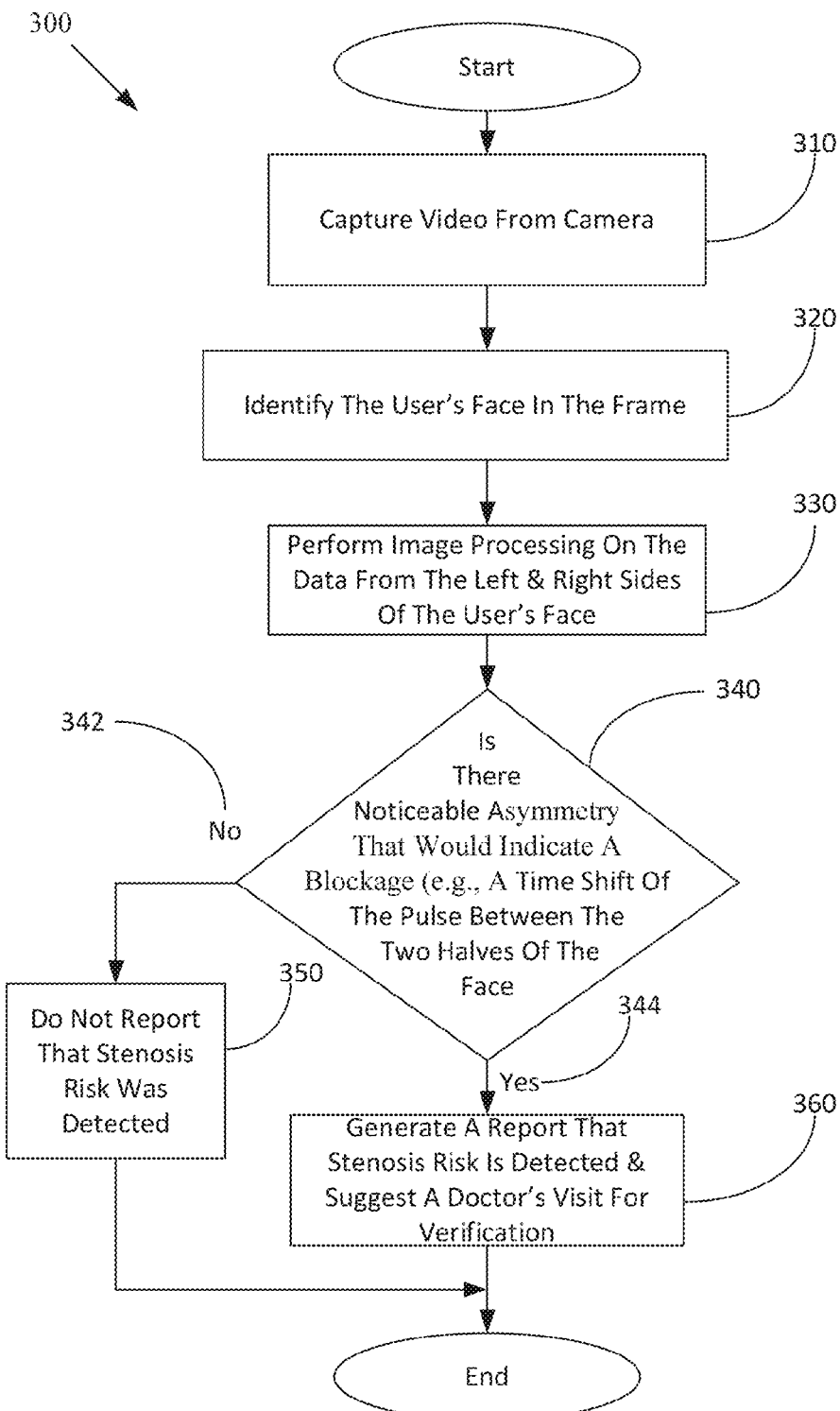
FIG. 3 illustrates a flowchart of a method for preliminary identification of carotid artery stenosis according to an embodiment.

FIG. 3 illustrates a flowchart of a method 300 for preliminary identification of carotid artery stenosis according to an embodiment. In FIG. 3, at block 310, video is captured from a camera that is focused on the face of a subject/user. In block 320, the face of the subject is identified in the frame of the camera. In block 330, image processing is performed on the data from the left side of the face of the subject and from the right side of the face of the subject. In block 340, a determination is made whether there is noticeable asymmetry that would indicate a blockage, e.g., a time shift of the pulse between the two halves of the face. If no noticeable asymmetry is detected 342, in block 350 stenosis risk detection is not reported. However, if a noticeable asymmetry is detected 344, in block 360 a report that a serious stenosis risk is generated and the subject may be referred to a doctor for verification.

Embodiments described herein involving processing image data form the left and right sides of a subjects face are not meant to be limiting. Rather, those skilled in the art will recognize that additional methods may be used to determine that the blood flow activity is asymmetric. For example, other characteristics of the pulse wave activity may be better indicators, wherein, instead of a delay being apparent on one side, the amplitude of one waveform may be detected simultaneously, but one of the pulses may be determined to be smaller thereby the pulse effect on one side of the face may be detected as being weaker. Accordingly, identification of the time shift is merely one method of determining the asymmetry.

Figure 4:
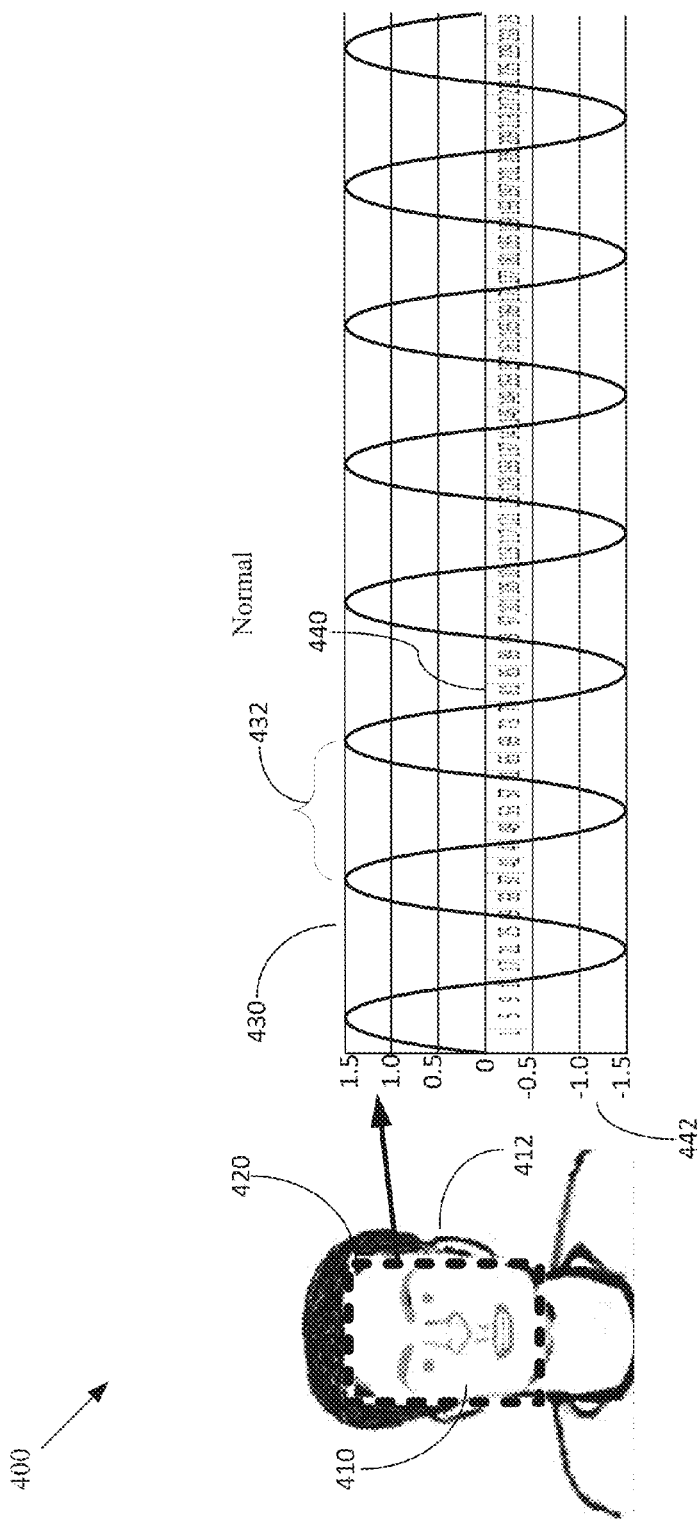
FIG. 4 illustrates facial video capture according to an embodiment.

FIG. 4 illustrates facial video capture 400 according to an embodiment. The face 410 of a subject 412 is shown identified in the frame 420 of the camera. Using visual computing techniques, a stenosis condition in one of the carotid arteries may be detected and an alert may be generated for the user to go see a doctor for verification and treatment. By monitoring the blood flow to the face 412 using camera-based methods, a telltale differential in pulse peak timing may be identified, which would indicate a stenosis condition in the carotid artery feeding one side of the face.

FIG. 4 also shows the video of the face 412 being used to derive a pulsing waveform 430 caused by the cardiac activity of the person imaged by tracking the minute color fluctuations caused when fresh blood arrives at the skin surface. Post-processing of the video stream of the face of the subject may be performed to identify facial pulse 432 of the subject. In FIG. 4, the X-axis 440 is time and the Y-axis 442 is the amount of the very small color intensity fluctuations, which oscillate around the average color of the subject's skin.

Figure 5:
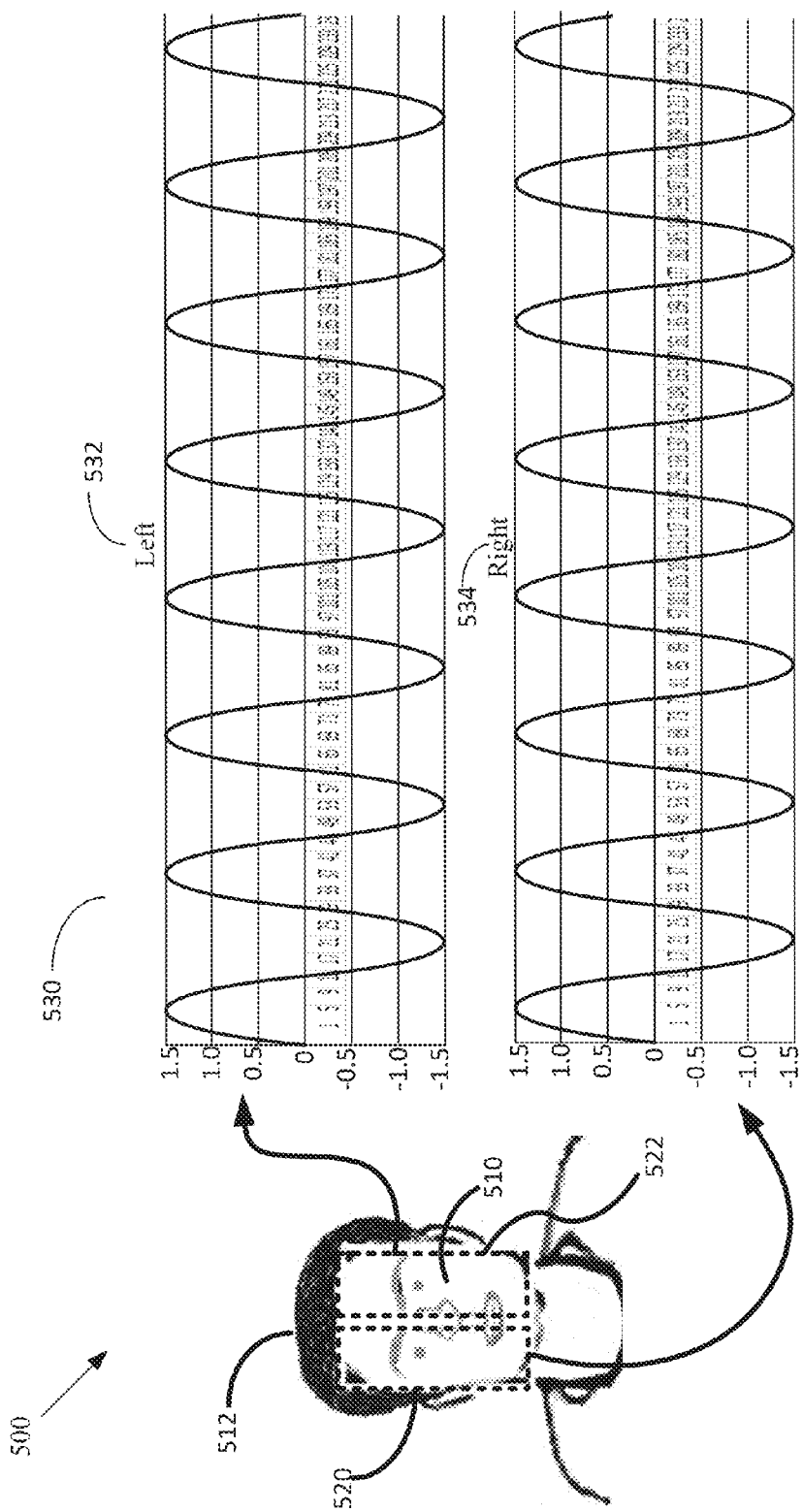
FIG. 5 shows two regions of interest of the face of the subject according to an embodiment.

FIG. 5 shows a subject having two regions of interest of the face shown 500 according to an embodiment. In FIG. 5, the face 510 of a subject 512 is shown identified in a left frame 520 of the camera on the right side of the subject's face 510 and a right frame 522 of the camera on the left side of the subject's face 510. Accordingly, distinct pulse waves 530 can be derived, i.e., a left pulsing waveform 532 associated with the left side of the face 522 of the subject 512 and a right pulsing waveform 534 associated with the right side of the face 520 of the subject 512. By taking advantage of the symmetric nature of the carotid arteries, which behave (for the most part) independently after branching from the aorta, independent waveforms may be recorded and observed for any asymmetry that would indicate a blockage somewhere along their paths.

Within the brain, there is a linkage between the left and right internal carotid structures, which is known as the Circle of Willis. One function of the Circle of Willis is to provide redundancy to attempt to redistribute blood flow in cases of stenosis describe herein. However, embodiments described herein do not discount the effect of the Circle of Willis. Rather, when the stenosis is pronounced, the ability of the Circle of Willis to redistribute blood flow from the unaffected arteries may not be sufficient to prevent the patient's stroke. Nevertheless, because embodiments described herein dealing with preventative screening, how well the Circle of Willis performs its functions does not matter. In any case, the Circle of Willis is a structure specifically linking the internal carotid arteries. The external carotid arteries, which feed the face and thus cause the waveforms being monitored are not linked and thus behave independently.

Figure 6:
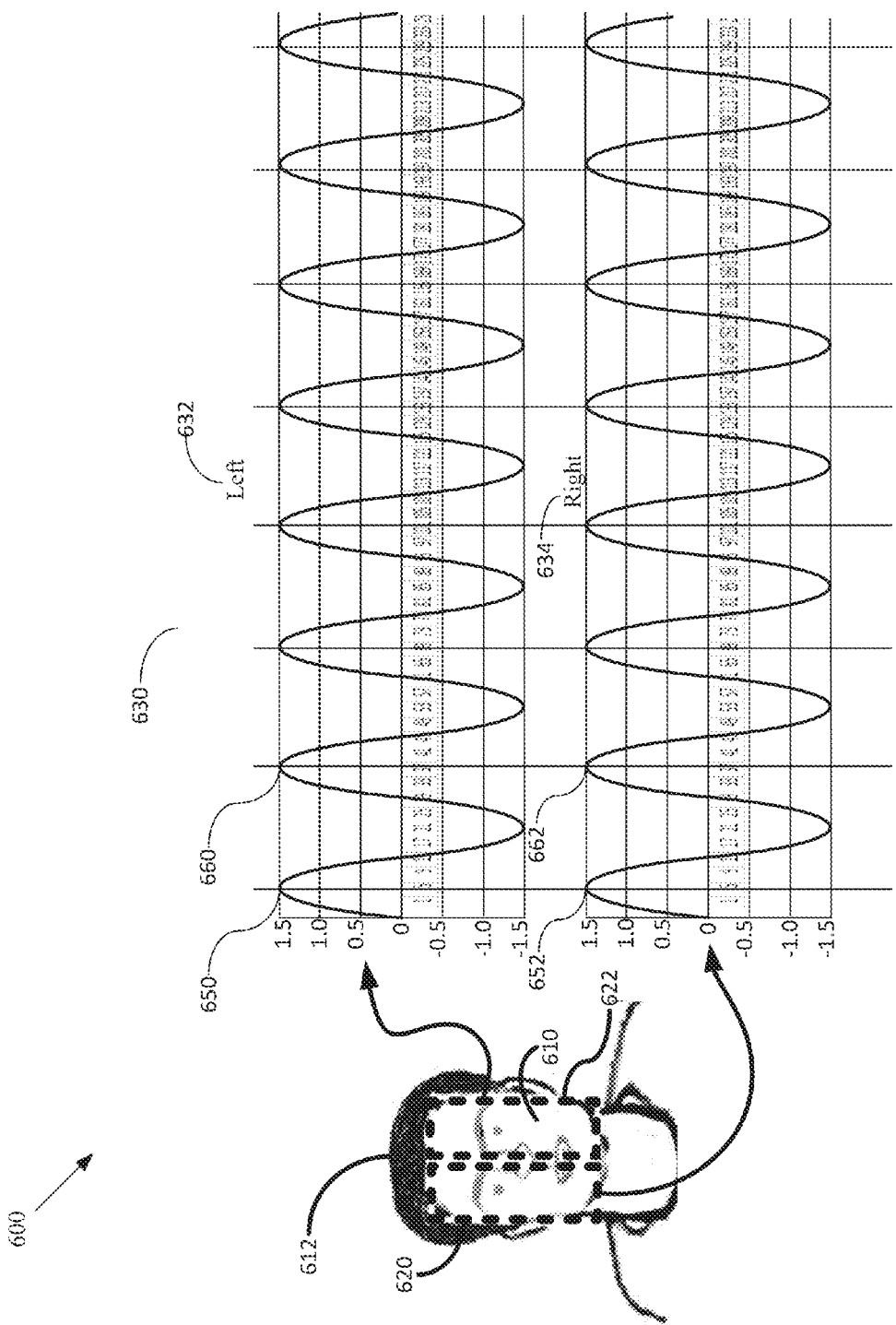
FIG. 6 shows an example of deriving pulsing waveforms caused by the cardiac activity of a healthy person according to an embodiment.

FIG. 6 shows an example of deriving pulsing waveforms caused by the cardiac activity of a healthy person 600 according to an embodiment. In FIG. 6, the face 610 of a subject 612 is shown identified in a left frame 620 of the camera on the right side of the subject's face 610 and a right frame 622 of the camera on the left side of the subject's face 610. Again, distinct pulse waves 630 can be derived, i.e., a left pulsing waveform 632 associated with the left side of the face 622 of the subject 612 and a right pulsing waveform 634 associated with the right side of the face 620 of the subject 612.

In a healthy subject, each pulse will arrive to the two sides of the face substantially simultaneously, so no time shift will be noticeable between the peaks 650, 652 or peaks 660, 662 of the two pulsing waveforms 632, 634. Accordingly, the phase of the left pulsing waveform 632 is synchronized with the phase of the right pulsing waveform 634. However, one skilled in the art will recognize that the peaks, e.g., peaks 650, 652 or peaks 660, 662, may exhibit a minute and insignificant phase shift and therefore may not be perfectly synchronized. Such a minute difference may be attributable to the anatomy of the subject, various system tolerances, etc.

Figure 7:
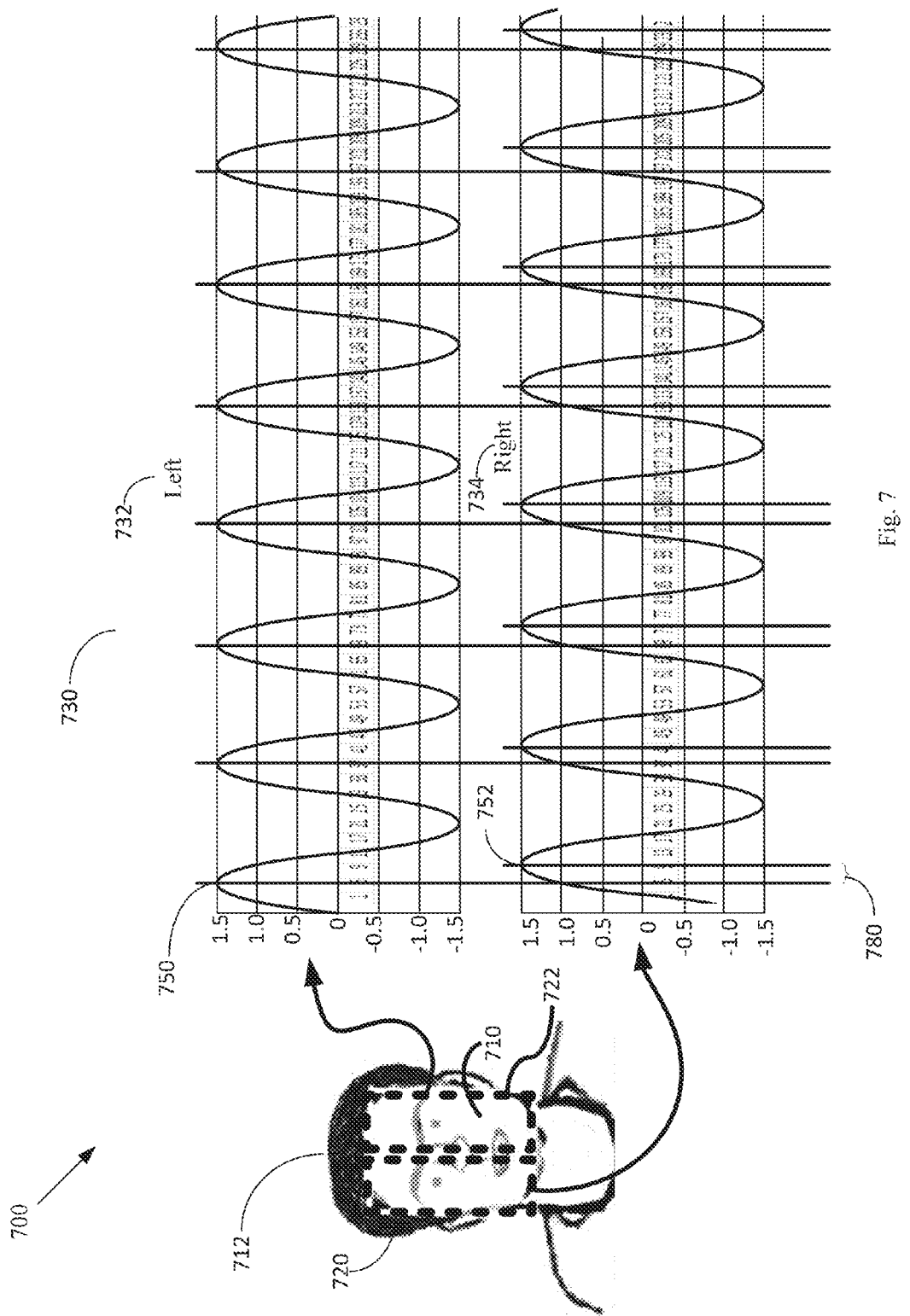
FIG. 7 illustrates pulsing waveforms of a subject caused by the cardiac activity of a person experiencing stenosis conditions according to an embodiment.

FIG. 7 illustrates pulsing waveforms of a subject caused by the cardiac activity of a person experiencing stenosis conditions 700 according to an embodiment. In FIG. 7, the face 710 of a subject 712 is again shown identified in a left frame 720 of the camera on the right side of the subject's face 710 and a right frame 722 of the camera on the left side of the subject's face 722. Again, distinct pulse waves 730 can be derived, i.e., a left pulsing waveform 732 associated with the left side of the face 722 of the subject 712 and a right pulsing waveform 734 associated with the right side of the face 720 of the subject 712.

The left pulsing waveform 732 and the right pulsing waveform 734 are processed to measure a time shift/phase shift 780 between the peak 750 of the first pulsing waveform 732 and the peak 752 of the second pulsing waveform 734. As shown in FIG. 7, the left pulsing waveform 732 peaks earlier than the right pulsing waveform 734. In FIG. 7, the left pulsing waveform 732 is leading the right pulsing waveform 734. This time shift/phase shift 780 is caused by the blockage in the artery that feeds one side of the face 710. Thus, the leading indicator for carotid artery stenosis may be determined to be exhibited when the phase shift 780 between the pulsing waveforms 732, 734 is greater than a nominal value. As mentioned above, the peaks, e.g., peaks 750, 752 or peaks 760, 762, may exhibit a minute and insignificant phase shift and therefore may not be perfectly synchronized due to various factors, such as the anatomy of the subject, various system tolerances, etc. Thus, the phase shift 780 may be compared to a predetermined value representative of carotid artery stenosis. When the phase shift 780 is greater than the predetermined value, the leading indicator for carotid artery stenosis is identified as being exhibited. For example, in FIG. 7, the phase shift 780 is approximately 5 frames. However, the predetermined value for identifying that the leading indicator for carotid artery stenosis is exhibited may be determined to be 0.1 frames, 0.75 frames, 1 frame, 2 frames, etc. The predetermined value may be derived through statistical analysis of carotid artery stenosis data, and may be refined over time. Thus, in FIG. 7, if the predetermined value for identifying that the leading indicator for carotid artery stenosis is exhibited is set at 2 frames, the phase shift 780 of approximately 5 frames would be identified as indicating carotid artery stenosis.

Figure 8:
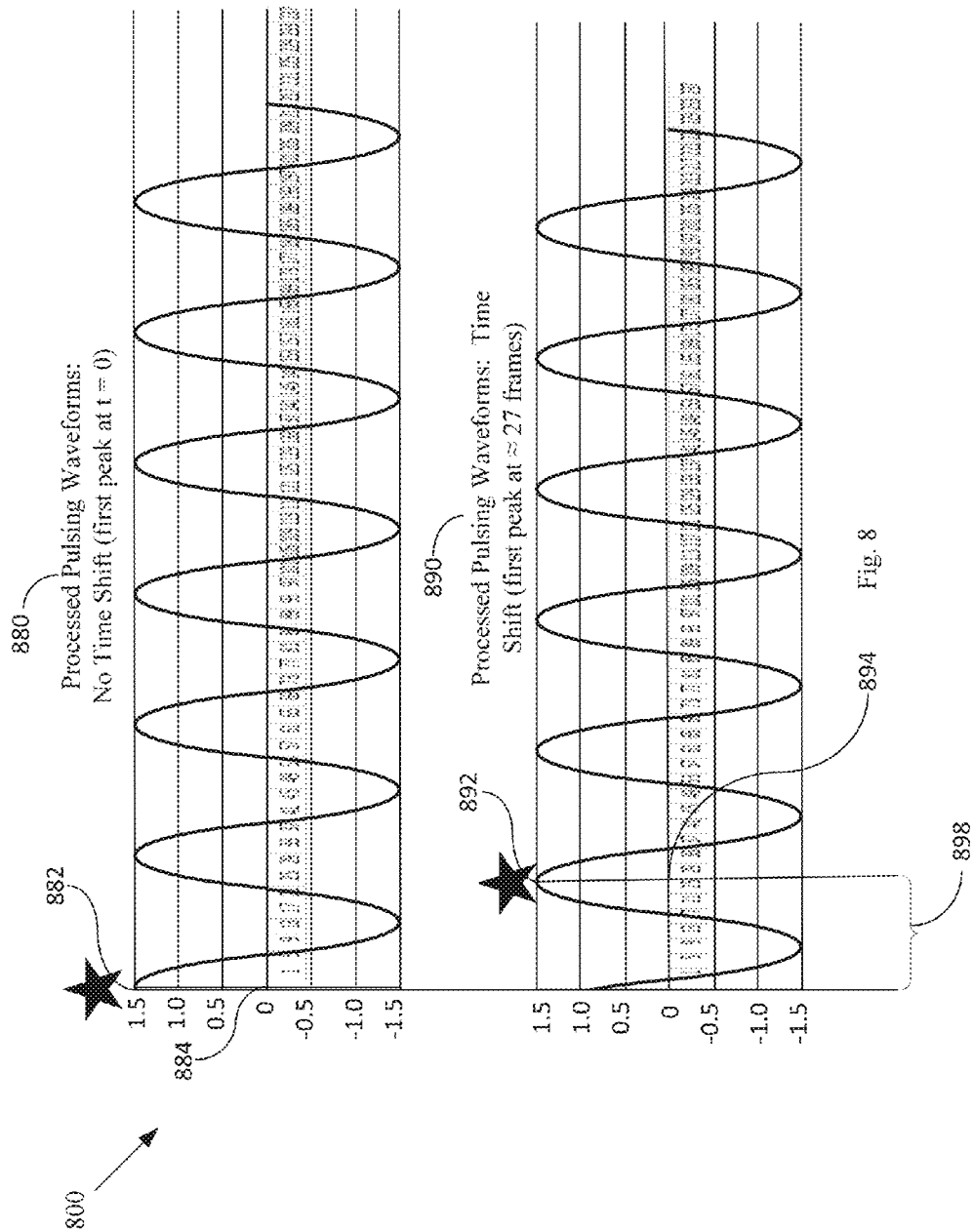
FIG. 8 is a detailed view of processed pulsing waveforms according to an embodiment.

FIG. 8 is a detailed view of processed pulsing waveforms 800 according to an embodiment. Common signal processing techniques, such as cross-correlation, can be applied to the left pulsing waveform and the right pulsing waveform to produce a processed waveform to identify if there is a asymmetry, e.g., a non-zero time delay between the two pulse events.

Cross-correlation is an operation where two signals are compared at a series of increasing offsets, e.g., moving the starting x value of where the start of one signal is positioned relative to the starting position of the other signal by increasing amounts, and then determining a value for how similar they are. FIG. 8 thus illustrates the resulting plot of similarity values, i.e., vertical axis, versus the amount of offset, i.e., horizontal axis.

In the special case of comparing two sinusoidal signals, their resulting cross-correlation will also end up being sinusoidal because as the two signals are offset more and more, their peaks will eventually line up again and their similarity measurement will peak again. As the offset increases, their similarity will be reduced and dip down until the signals are entirely in opposite phase, but will increase again once the offset is enough to have the next set of peaks line up.

In FIG. 8, the waveform 880 is the result of performing a cross-correlation operation on the two waveforms from FIG. 6, i.e., the healthy case. Because they start out with their peaks lined up, they will have a maximum similarity peak 882 at offset=0, noted as "t".

In contrast, the wave marked 890 is the result of cross-correlating waveforms similar to those illustrated in FIG. 7, i.e., an unhealthy case. An offset is introduced to one of the signals before their peaks line up fully represented by peak 892. As shown in FIG. 8, the amount of offset 898, t=27 frames 894, identifies how much of a time shift is present between the two signals, e.g., the waveform associated with the left side of the face and the waveform associated with the right side of the face.

Figure 9:
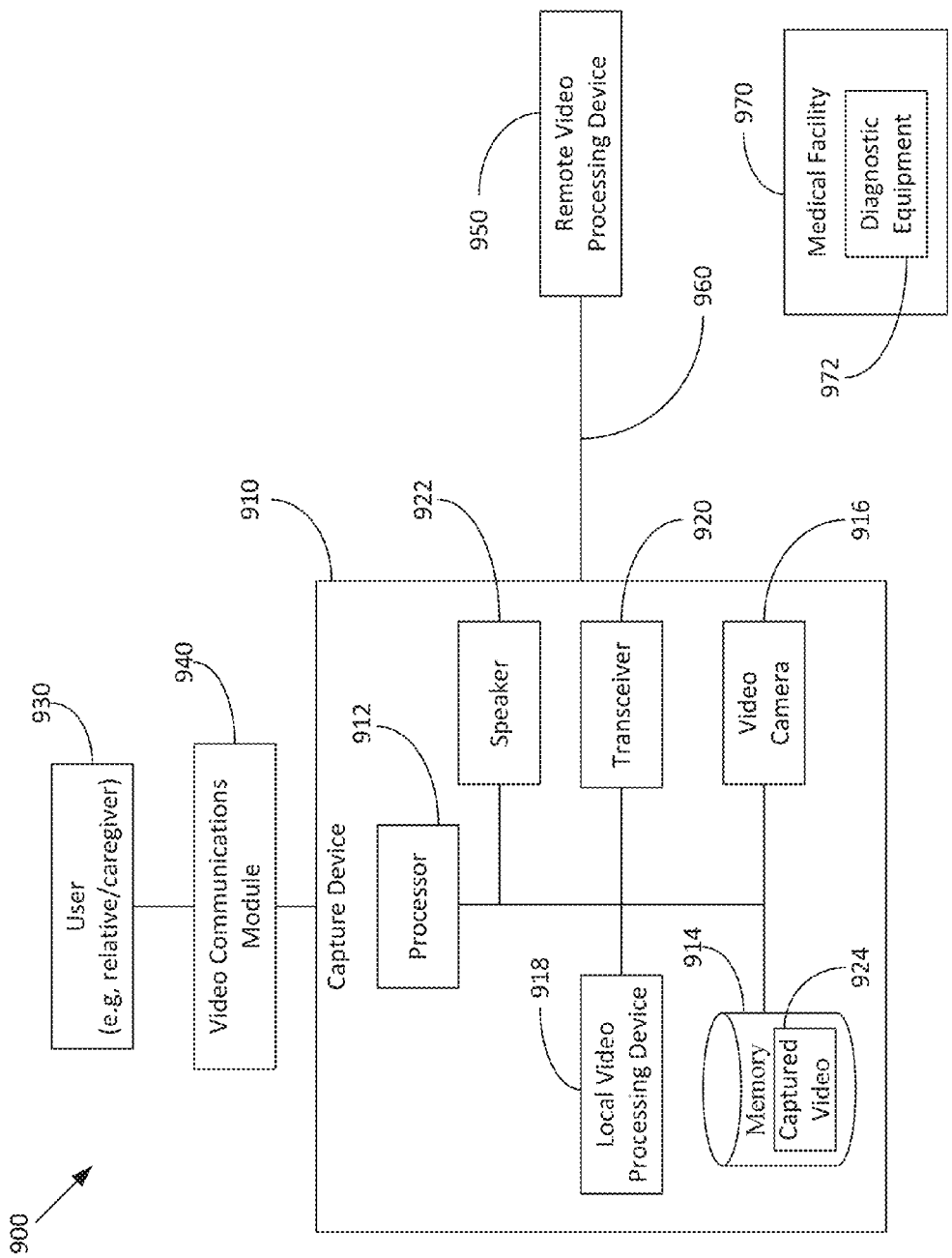
FIG. 9 illustrates a system for detecting a leading indicator for carotid artery stenosis according to an embodiment.

FIG. 9 illustrates a system 900 for detecting a leading indicator for carotid artery stenosis according to an embodiment. The system 900 includes a video capture device 910. The capture device 910 may be operated by a user 930, such as a patient, caregiver, friend, relative, etc. The user 930 may be local or remote from the subject. The capture device 910 may include a processor 912, memory 914, a video camera 916, a local video processing device 918 and a transceiver 920. The video camera 916 may be focused on the face of the subject as described above. The subject may orient the capturer device 910 including the video camera 916 as needed or a user 930 that is local may orient the capturer device 910 and video camera 924. When the user 930 is remote, the user 930 may provide audio instructions to the subject via speaker 922 to aid in orienting the capture device 910 and video camera 916.

Once the video camera 916 has captured a video and the captured video 924 has been stored in memory 914, processor 912 may initiate video processing of the captured video 924 locally by video processing device 918 or the captured video 924 in memory 914 may be sent to remote video processing device 950. Transceiver 920 may communicate with remote video processing device 950 via the Internet, a cellular communications network, or other type of communications network 960. The remote video processor 950 and/or the local video processing device 918 may provide data associated with the processing of the captured video 924 so that the subject may be informed that a carotid artery stenosis event has been detected or that no carotid artery stenosis event has been detected. For example, the processor 912 may be arranged to measure a phase shift between the peak of a first pulsing waveform associated with video of the right side of the face of the subject and the peak of the second pulsing waveform associated with video of the left side of the face of the subject. The processor 912 may be arranged to determine the leading indicator for carotid artery stenosis is exhibited when a phase shift between the first pulsing waveform and the second pulsing waveform exceeds a predetermined value.

As mentioned earlier above, because the US Preventative Services Task Force does not recommend preventative screening for carotid artery stenosis, it is often the case that the condition remains undiagnosed until the subject has their first stroke event, which is hopefully minor and brief. A transient episode of neurologic dysfunction caused by ischemia, i.e., loss of blood flow, is referred to as a transient ischemic attack. A transient ischemic attack is commonly characterized by temporary loss of vision or slurred speech, among other symptoms.

FIG. 9 also shows a medical facility 970 where a user may obtain more detailed medical diagnosis using diagnostic equipment 972 of the medical facility 970. At this point, medical services providers may use the diagnostic equipment 972, e.g., duplex ultrasound, magnetic resonance imaging (MRI), etc., to analyze the internal structure of the left and right carotid arteries to determine if there is a blockage in one or the other. Thereafter, treatment may be prescribed by a doctor after reviewing the diagnostic report provided by the diagnostic equipment 972 of the medical facility 970 to prevent a second event.

Using this method, an undiagnosed condition can be recognized at home or potentially anywhere when a video camera 916 may capture video of the face of the subject. Because the system uses a common webcam, the system can be distributed at negligible expense, or even built into camera-enabled mobile devices. Subjects may periodically use the system to preventatively examine themselves or their loved ones.

The video processing device 918, 950 may generate false positive conditions, i.e., when the system reports a stenosis condition that is not actually present. However, false positive conditions would be very rare because that would somehow involve a subject having very different pulse activity on the two sides of their face that is somehow not caused by stenosis. The video processing 918, 950 may also generate false negative conditions, i.e., when the system does not successfully report a stenosis condition that the subject actually does have. However, this would put the subject in no more risk than they would otherwise be because doctors do not typically test for the condition in otherwise asymptomatic subjects. Accordingly, the system 900 according to an embodiment is considered an early-warning tool that can identify a significant stenosis risk.

For example, a relative or caregiver, e.g., a user 930, may visit the subject, or the user 930 may use Skype™ or another video communications module 940 to contact a homebound subject. Such contact may be based on the subject complaining about some weakness and numbness on one side of the face of the subject or may be part of a routine checkup. When the user 930 visits the subject, the relative/caregiver uses the system to obtain an incoming video feed and capture a short video for processing. If the user 930 is to make remote contact with the subject, the user 930 may have the subject sit in front of a laptop or other video capture device 910, while the user 930 operates the system to capture video of the subject. The system 900 may generate a report that there is a pronounced asymmetry in the heart beat between the two sides of the face of the subject and suggests a visit to the doctor for examination. At the doctor's office, the doctor may be able to quickly verify a significant blockage of the subject and prescribe a course of action to prevent further buildup. Alternatively, in more severe situations, the doctor may order surgery to clear the blockage thus averting the risk of an unexpected stroke.

The video processing device 918 may identify a difference in pulse activity between the two sides of the face. Calibration of the system 900 may be implemented by generating a sample video feed in which asymmetry is present, e.g., one half of the face has been delayed by a number of frames, and presenting the video feed to the video processing device 918. A stenosis condition would be detected when the video processing device 918 is supplied this doctored video as input.

Figure 10:
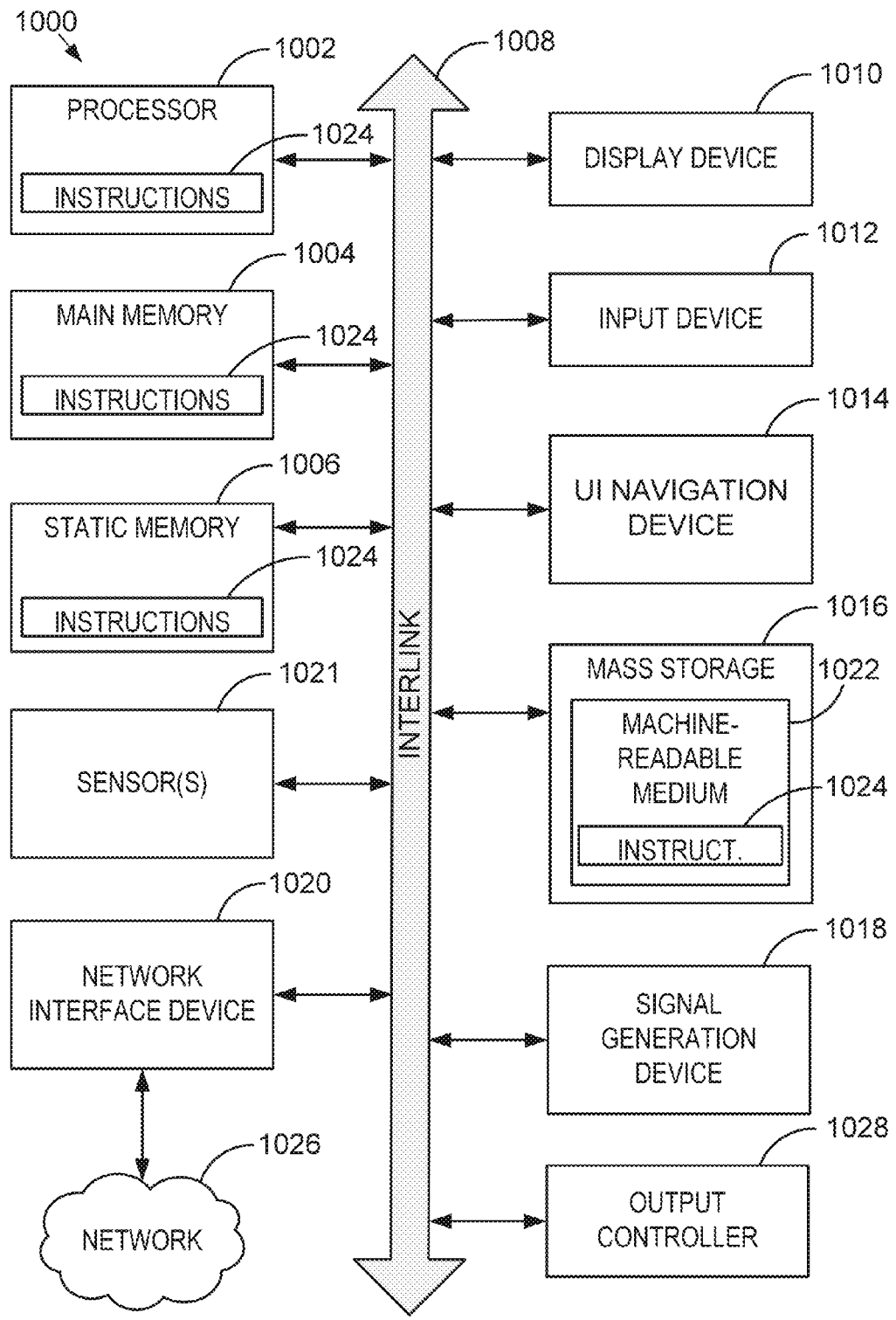
FIG. 10 illustrates a block diagram of an example machine for detecting a leading stroke risk indicator using low-cost, non-contact visual computing methods according to an embodiment.

FIG. 10 illustrates a block diagram of an example machine 1000 for detecting a leading stroke risk indicator using low-cost, non-contact visual computing methods, according to an embodiment, upon which any one or more of the techniques (e.g., methodologies) discussed herein may perform. In alternative embodiments, the machine 1000 may operate as a standalone device or may be connected (e.g., networked) to other machines. In a networked deployment, the machine 1000 may operate in the capacity of a server machine and/or a client machine in server-client network environments. In an example, the machine 1000 may act as a peer machine in peer-to-peer (P2P) (or other distributed) network environment. The machine 1000 may be a personal computer (PC), a tablet PC, a set-top box (STB), a Personal Digital Assistant (PDA), a mobile telephone, a web appliance, a network router, switch or bridge, or any machine capable of executing instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate on, logic or a number of components, modules, or mechanisms. A "module" is a self-contained functional component. A module may be implemented in hardware, software, firmware, or any combination thereof. A software module is a collection of software components and data structures that performs a particular task or implements a particular abstract data type. A hardware-implemented module is tangible unit capable of performing certain operations and may be configured or arranged in a certain manner. In example embodiments, one or more computer systems (e.g., a standalone, client or server computer system) or one or more processors may be configured by software (e.g., an application or application portion) as a hardware-implemented module that operates to perform certain operations as described herein.

In an example, at least a part of one or more computer systems (e.g., a standalone, client or server computer system) or one or more hardware processors 1002 may be configured by firmware or software (e.g., instructions, an application portion, or an application) as a module that operates to perform specified operations. In an example, the software may reside on at least one machine readable medium. In an example, the software, when executed by the underlying hardware of the module, causes the hardware to perform the specified operations.

Accordingly, the term "module" is understood to encompass a tangible entity, be that an entity that is physically constructed, specifically configured (e.g., hardwired), or temporarily (e.g., transitorily) configured (e.g., programmed) to operate in a specified manner or to perform at least part of any operation described herein. Considering examples in which modules are temporarily configured, a module need not be instantiated at any one moment in time. For example, where the modules comprise a general-purpose hardware processor 1002 configured using software; the general-purpose hardware processor may be configured as respective different modules at different times. Software may accordingly configure a hardware processor, for example, to constitute a particular module at one instance of time and to constitute a different module at a different instance of time. The term "application," or variants thereof, is used expansively herein to include routines, program modules, programs, components, and the like, and may be implemented on various system configurations, including single-processor or multiprocessor systems, microprocessor-based electronics, single-core or multi-core systems, combinations thereof, and the like. Thus, the term application may be used to refer to an embodiment of software or to hardware arranged to perform at least part of any operation described herein.

Machine (e.g., computer system) 1000 may include a hardware processor 1002 (e.g., a central processing unit (CPU), a graphics processing unit (GPU), a hardware processor core, or any combination thereof), a main memory 1004 and a static memory 1006, at least some of which may communicate with others via an interlink (e.g., bus) 1008. The machine 1000 may further include a display unit 1010, an alphanumeric input device 1012 (e.g., a keyboard), and a user interface (UI) navigation device 1014 (e.g., a mouse).

In an example, the display unit 1010, input device 1012 and UI navigation device 1014 may be a touch screen display. The machine 1000 may additionally include a storage device (e.g., drive unit) 1016, a signal generation device 1018 (e.g., a speaker), a network interface device 1020, and one or more sensors 1021, such as a global positioning system (GPS) sensor, compass, accelerometer, or other sensor. The machine 1000 may include an output controller 1028, such as a serial (e.g., universal serial bus (USB), parallel, or other wired or wireless (e.g., infrared (IR)) connection to communicate or control one or more peripheral devices (e.g., a printer, card reader, etc.).

The storage device 1016 may include at least one machine readable medium 1022 on which is stored one or more sets of data structures or instructions 1024 (e.g., software) embodying or utilized by any one or more of the techniques or functions described herein. The instructions 1024 may also reside, at least partially, additional machine readable memories such as main memory 1004, static memory 1006, or within the hardware processor 1002 during execution thereof by the machine 1000. In an example, one or any combination of the hardware processor 1002, the main memory 1004, the static memory 1006, or the storage device 1016 may constitute machine readable media.

While the machine readable medium 1022 is illustrated as a single medium, the term "machine readable medium" may include a single medium or multiple media (e.g., a centralized or distributed database, and/or associated caches and servers) that configured to store the one or more instructions 1024.

The term "machine readable medium" may include any medium that is capable of storing, encoding, or carrying instructions for execution by the machine 1000 and that cause the machine 1000 to perform any one or more of the techniques of the present disclosure, or that is capable of storing, encoding or carrying data structures used by or associated with such instructions. Non-limiting machine readable medium examples may include solid-state memories, and optical and magnetic media. Specific examples of machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 1024 may further be transmitted or received over a communications network 1026 using a transmission medium via the network interface device 1020 utilizing any one of a number of transfer protocols. Example communication networks may include a local area network (LAN), a wide area network (WAN), a packet data network (e.g., the Internet), mobile telephone networks ((e.g., channel access methods including Code Division Multiple Access (CDMA), Time-division multiple access (TDMA), Frequency-division multiple access (FDMA), and Orthogonal Frequency Division Multiple Access (OFDMA) and cellular networks such as Global System for Mobile Communications (GSM), Universal Mobile Telecommunications System (UMTS), CDMA 2000 1x* standards and Long Term Evolution (LTE)), Plain Old Telephone (POTS) networks, and wireless data networks (e.g., Institute of Electrical and Electronics Engineers (IEEE) 802 family of standards including IEEE 802.11 standards (WiFi), IEEE 802.16 standards (WiMax®) and others), peer-to-peer (P2P) networks, or other protocols now known or later developed.

For example, the network interface device 1020 may include one or more physical jacks (e.g., Ethernet, coaxial, or phone jacks) or one or more antennas to connect to the communications network 1026. In an example, the network interface device 1020 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 1000, and includes digital or analog communications signals or other intangible medium to facilitate communication of such software.

ADDITIONAL NOTES & EXAMPLES

Example 1 may include subject matter (such as a device, apparatus, client or system) including a video camera arranged to capture a video of a face of a subject to be evaluated for having a stroke risk indicator, a memory for storing data therein and a processor, coupled to the memory, the processor arranged to process the video of the face of the subject to produce a first pulse waveform associated with a pulse of a right side of the face of the subject and to produce a second pulse waveform associated with a pulse of a left side of the face of the subject, the processor further arranged to analyze the first and second pulse waveforms to determine whether the video of the face of the subject exhibits a leading indicator for carotid artery stenosis.

Example 2 may optionally include the subject matter of Example 1, further comprising a local video processing device, the local video processing device arranged to perform image processing of the video of the face of the subject captured by the video camera to produce the first and second pulse waveforms.

Example 3 may optionally include the subject matter of Example 1 or 2, further comprising a transceiver, the transceiver arranged to forward the video of the face of the subject captured by the video camera to a remote video processing device, the remote video processing device to perform image processing of the forwarded video of the face of the subject to produce the first and second pulse waveforms and to forward the first and second pulse waveforms to the processor.

Example 4 may optionally include the subject matter of one or more of Examples 1-3, wherein the memory is arranged to store the captured video.

Example 5 may optionally include the subject matter of one or more of Examples 1-4, wherein the first and second pulse waveforms comprise processed image data.

Example 6 may optionally include the subject matter of one or more of Examples 1-5, wherein the processor is further arranged to identify a first characteristics of the first pulse waveform associated with the right side of the face of the subject for detecting carotid artery stenosis and to identify a second characteristics of the second pulse waveform associated with the left side of the face of the subject for detecting carotid artery stenosis.

Example 7 may optionally include the subject matter of one or more of Examples 1-6, wherein the first characteristics is a peak of the first pulse waveform for the right side of the face of the subject and the second characteristics is a peak of the second pulse waveform for the left side of the face of the subject, the processor being arranged to measure a phase shift between the peak of the first pulse waveform and the peak of the second pulse waveform and to determine the leading indicator for carotid artery stenosis is exhibited when the phase shift exceeds a predetermined value.

Example 8 may optionally include the subject matter of one or more of Examples 1-7, wherein the first and second pulse waveforms are processed by the processor to cross-correlate the first and second pulse waveforms to identify a degree of similarity between the first and second pulse waveform for determining whether the video of the face of the subject exhibits a leading indicator for carotid artery stenosis.

Example 9 may optionally include the subject matter of one or more of Examples 1-8, wherein the video camera provides video data to a remote user via a video communications module.

Example 10 may optionally include the subject matter of one or more of Examples 1-9, further comprising a speaker, wherein the remote user uses the provided video data to provide audio instructions to the subject via the speaker.

Example 11 includes subject matter (such as a method or means for performing acts) for capturing, at a video capture device, a video of a face of a subject to be evaluated for exhibition of a leading indicator for carotid artery stenosis, processing, by a video image processor, the video of the face of the subject to produce a first pulse waveform associated with a pulse of a right side of the face of the subject and to produce a second pulse waveform associated with a pulse of a left side of the face of the subject, analyzing the first and second pulse waveforms to determine whether the video of the face of the subject exhibits a leading indicator for carotid artery stenosis and generating a report indicating stenosis risk is detected and suggesting the subject visit a doctor for verification when the analysis of the first and second pulse waveforms are determined to exhibit the leading indicator for carotid artery stenosis.

Example 12 may optionally include the subject matter of Example 11, further comprising performing, local to the subject, image processing of the captured video to produce the first and second waveforms.

Example 13 may optionally include the subject matter of Example 11 or 12, further comprising transmitting, from the video capture device, the captured video of the face of the subject to a remote video processing device, performing image processing of the captured video of the face of the subject at the remote video processing device to produce the first and second pulse waveforms and transmitting the first and second pulse waveforms to the video capture device.

Example 14 may optionally include the subject matter of one or more of Examples 11-13, further comprising storing the captured video in memory at the video capture device.

Example 15 may optionally include the subject matter of one or more of Examples 11-14, wherein the capturing the video of the face of the subject comprises capturing video of the right side and the left side of the face of the subject.

Example 16 may optionally include the subject matter of one or more of Examples 11-15, wherein the analyzing the first and second pulse waveforms to determine whether the video of the face of the subject exhibits a leading indicator for carotid artery stenosis further comprises identifying a peak of the first pulse waveform for the right side of the face of the subject, identifying a peak of the second pulse waveform for the left side of the face of the subject, measuring a phase shift between the peak of the first pulsing waveform and the peak of the second pulsing waveform and determining the leading indicator for carotid artery stenosis is exhibited when the phase shift exceeds a predetermined value.

Example 17 may optionally include the subject matter of one or more of Examples 11-16, wherein the analyzing the first and second pulse waveforms to determine whether the video of the face of the subject exhibits a leading indicator for carotid artery stenosis further comprises processing the first and second pulse waveforms to cross-correlate the first pulse waveform with the second pulsing waveform to identify a degree of similarity between the first and second pulse waveforms for determining whether the video of the face of the subject exhibits a leading indicator for carotid artery stenosis.

Example 18 may optionally include the subject matter of one or more of Examples 11-17, further comprising providing video data from the video capture device to a remote user via a video communications module and providing audio instructions to the subject via a speaker based on the video data provided to the remote user via the video communications module.

Example 19 may include subject matter (such as means for performing acts or machine readable medium including instructions that, when executed by the machine, cause the machine to perform acts) including capturing, at a video capture device, a video of a face of a subject to be evaluated for exhibition of a leading indicator for carotid artery stenosis, processing, by a video image processor, the video of the face of the subject to produce a first pulse waveform associated with a pulse of a right side of the face of the subject and to produce a second pulse waveform associated with a pulse of a left side of the face of the subject, analyzing the first and second pulse waveforms to determine whether the video of the face of the subject exhibits a leading indicator for carotid artery stenosis and generating a report indicating stenosis risk is detected and suggesting the subject visit a doctor for verification when the analysis of the first and second pulse waveforms are determined to exhibit the leading indicator for carotid artery stenosis.

Example 20 may optionally include the subject matter of Example 19, further comprising performing, local to the subject, image processing of the captured video to produce the first and second waveforms.

Example 21 may optionally include the subject matter of one or more of Examples 19 or 20, further comprising transmitting, from the video capture device, the captured video of the face of the subject to a remote video processing device, performing image processing of the captured video of the face of the subject at the remote video processing device to produce the first and second pulse waveforms and transmitting the first and second pulse waveforms to the video capture device.

Example 22 may optionally include the subject matter of one or more of Examples 19-21, wherein the capturing the video of the face of the subject comprises capturing video of the right side and the left side of the face of the subject.

Example 23 may optionally include the subject matter of one or more of Examples 19-22, wherein the analyzing the first and second pulse waveforms to determine whether the video of the face of the subject exhibits a leading indicator for carotid artery stenosis further comprises identifying a peak of the first pulse waveform for the right side of the face of the subject, identifying a peak of the second pulse waveform for the left side of the face of the subject, measuring a phase shift between the peak of the first pulsing waveform and the peak of the second pulsing waveform and determining the leading indicator for carotid artery stenosis is exhibited when the phase shift exceeds a predetermined value.

Example 24 may optionally include the subject matter of one or more of Examples 19-23, wherein the analyzing the first and second pulse waveforms to determine whether the video of the face of the subject exhibits a leading indicator for carotid artery stenosis further comprises processing the first and second pulse waveforms to cross-correlate the first pulse waveform with the second pulsing waveform to identify a degree of similarity between the first and second pulse waveforms for determining whether the video of the face of the subject exhibits a leading indicator for carotid artery stenosis.

Example 25 may optionally include the subject matter of one or more of Examples 19-24, further comprising further comprising providing video data from the video capture device to a remote user via a video communications module and providing audio instructions to the subject via a speaker based on the video data provided to the remote user via the video communications module.

The above detailed description includes references to the accompanying drawings, which form a part of the detailed description. The drawings show, by way of illustration, specific embodiments that may be practiced. These embodiments are also referred to herein as "examples." Such examples may include elements in addition to those shown or described. However, also contemplated are examples that include the elements shown or described. Moreover, also contemplate are examples using any combination or permutation of those elements shown or described (or one or more aspects thereof), either with respect to a particular example (or one or more aspects thereof), or with respect to other examples (or one or more aspects thereof) shown or described herein.

Publications, patents, and patent documents referred to in this document are incorporated by reference herein in their entirety, as though individually incorporated by reference. In the event of inconsistent usages between this document and those documents so incorporated by reference, the usage in the incorporated reference(s) are supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to suggest a numerical order for their objects.

The above description is intended to be illustrative, and not restrictive. For example, the above-described examples (or one or more aspects thereof) may be used in combination with others. Other embodiments may be used, such as by one of ordinary skill in the art upon reviewing the above description. The Abstract is to allow the reader to quickly ascertain the nature of the technical disclosure, for example, to comply with 37 C.F.R. §1.72(b) in the United States of America. It is submitted with the understanding that it will not be used to interpret or limit the scope or meaning of the claims. Also, in the above Detailed Description, various features may be grouped together to streamline the disclosure. However, the claims may not set forth features disclosed herein because embodiments may include a subset of said features. Further, embodiments may include fewer features than those disclosed in a particular example. Thus, the following claims are hereby incorporated into the Detailed Description, with a claim standing on its own as a separate embodiment. The scope of the embodiments disclosed herein is to be determined with reference to the appended claims, along with the full scope of equivalents to which such claims are entitled.

What is claimed is:

1. A device for detecting a leading stroke risk indicator, comprising:
    a video camera configured to capture a video of a face of a subject to be evaluated for having a stroke risk indicator;
    a memory for storing the video; and
    a processor, coupled to the memory, the processor configured to:
        process the video to produce a first pulse waveform associated with a pulse of a right side of the face of the subject and to produce a second pulse waveform associated with a pulse of a left side of the face of the subject;
        identify a peak of the first pulse waveform and identify a peak of the second pulse waveform;
        analyze the first and second pulse waveforms to measure a phase shift between the peak of the first pulse waveform and the peak of the second pulse waveform; and
        determine whether the subject exhibits a leading indicator for carotid artery stenosis based on the phase shift.

2. The device of claim 1, the processor comprising a local video processing device configured to perform image processing of the video to produce the first and second pulse waveforms.

3. The device of claim 1 further comprising a transceiver, the transceiver configured to forward the video to the processor, the processor comprising a remote video processing device, the remote video processing device to perform image processing of the forwarded video to produce the first and second pulse waveforms.

4. The device of claim 1, wherein the processor is configured to determine the leading indicator for carotid artery stenosis is exhibited when the phase shift exceeds a predetermined value.

5. The device of claim 1, wherein the first and second pulse waveforms are processed by the processor to cross-correlate the first and second pulse waveforms to measure the phase shift.

6. The device of claim 1, wherein the video camera provides video data to a remote user via a video communications module.

7. The device of claim 6 further comprising a speaker, wherein the remote user uses the provided video data to provide audio instructions to the subject via the speaker.

8. A method fur detecting a leading stroke risk indicator, comprising:
    capturing, at a video capture device, a video of a face of a subject;
    processing, by a video image processor, the video to produce a first pulse waveform associated with a pulse of a right side of the face of the subject and to produce a second pulse waveform associated with a pulse of a left side of the face of the subject;

identifying a peak of the first pulse waveform and a peak of the second pulse waveform;

analyzing the first and second pulse waveforms to measure a phase shift between the peak of the first pulse waveform and the peak of the second pulse waveform; and determining whether the subject exhibits a leading indicator for carotid artery stenosis based on the phase shift; and generating a report indicating stenosis risk is detected and suggesting the subject visit a doctor for verification when the analysis of the first and second pulse waveforms determines that the subject exhibits the leading indicator for carotid artery stenosis.

9. The method of claim 8, the processing comprising performing, local to the subject, image processing of the captured video to produce the first and second waveforms.

10. The method of claim 8 further comprising transmitting, from the video capture device, the video to a remote video processing device;
wherein the processing comprises performing image processing of the captured video of the face of the subject at the remote video processing device to produce the first and second pulse waveforms.

11. The method of claim 8 further comprising storing the captured video in memory at the video capture device.

12. The method of claim 8, further comprising determining the leading indicator for carotid artery stenosis is exhibited when the phase shift exceeds a predetermined value.

13. The method of claim 8, further comprising processing the first and second pulse waveforms to cross-correlate the first pulse waveform with the second pulse waveform to measure the phase shift.

14. The method of claim 8 further comprising providing video data from the video capture device to a remote user via a video communications module and providing audio instructions to the subject via a speaker based on the video data provided to the remote user via the video communications module.

15. At least one non-transitory machine readable medium comprising instructions that, when executed by the machine, cause the machine to perform operations for detecting a leading stroke risk indicator, the operations comprising:
capturing, at a video capture device, a video of a face of a subject;
processing, by a video image processor, the video of the face of the subject to produce a first pulse waveform associated with a pulse of a right side of the face of the subject and to produce a second pulse waveform associated with a pulse of a left side of the face of the subject;
identifying a peak of the first pulse waveform and a peak of the second pulse waveform;
analyzing the first and second pulse waveforms to measure a phase shift between the peak of the first pulse waveform and the peak of the second pulse waveform; and
determining whether the subject exhibits a leading indicator for carotid artery stenosis based on the phase shift; and
generating a report indicating stenosis risk is detected and suggesting the subject visit a doctor for verification when the analysis of the first and second pulse waveforms determines that the subject exhibits the leading indicator for carotid artery stenosis.

16. The at least one non-transitory machine readable medium of claim 15, the processing comprising performing, local to the subject, image processing of the captured video to produce the first and second waveforms.

17. The at least one non-transitory machine readable medium of claim 15 further comprising transmitting, from the video capture device, the video to a remote video processing device;
wherein the processing comprises performing image processing of the captured video of the face of the subject at the remote video processing device to produce the first and second pulse waveforms.

18. The at least one non-transitory machine readable medium of claim 15, the operations further comprising determining the leading indicator for carotid artery stenosis is exhibited when the phase shift exceeds a predetermined value.

19. The at least one non-transitory machine readable medium of claim 15, the operations further comprising processing the first and second pulse waveforms to cross-correlate the first pulse waveform with the second pulse waveform to measure the phase shift.

20. The at least one non-transitory machine readable medium of claim 15 further comprising providing video data from the video capture device to a remote user via a video communications module and providing audio instructions to the subject via a speaker based on the video data provided to the remote user via the video communications module.

* * * * *

UNITED STATES PATENT AND TRADEMARK OFFICE
CERTIFICATE OF CORRECTION

PATENT NO. : 9,579,067 B2
APPLICATION NO. : 14/125422
DATED : February 28, 2017
INVENTOR(S) : Jonathan Moisant Thompson Page 1 of 1

It is certified that error appears in the above-identified patent and that said Letters Patent is hereby corrected as shown below:

On the Title Page

In item (71), in "Applicant", in Column 1, Line 1, delete "Jonathan Moisant Thompson," and insert --Intel Corporation,-- therefor In the Claims In Column 14, Line 61, in Claim 8, delete "fur" and insert --for-- therefor Signed and Sealed this
Fourth Day of June, 2019

Andrei Iancu
*Director of the United States Patent and Trademark Office*